(12) United States Patent
Maesani et al.

(10) Patent No.: US 11,478,632 B2
(45) Date of Patent: Oct. 25, 2022

(54) ELECTRODE AND CONNECTOR ASSEMBLIES FOR NON-INVASIVE TRANSCUTANEOUS ELECTRICAL STIMULATION AND BIOLOGICAL SIGNAL SENSING

(71) Applicant: INTENTO SA, Ecublens (CH)

(72) Inventors: Andrea Maesani, Lausanne (CH); Alice Tonazzini, Neuchatel (CH)

(73) Assignee: MINDMAZE GROUP SA, Lausanne (CH)

( * ) Notice: Subject to any disclaimer, the term of this patent is extended or adjusted under 35 U.S.C. 154(b) by 472 days.

(21) Appl. No.: 16/470,555

(22) PCT Filed: Dec. 19, 2017

(86) PCT No.: PCT/IB2017/058136
§ 371 (c)(1),
(2) Date: Jun. 18, 2019

(87) PCT Pub. No.: WO2018/116161
PCT Pub. Date: Jun. 28, 2018

(65) Prior Publication Data
US 2019/0344069 A1    Nov. 14, 2019

(30) Foreign Application Priority Data
Dec. 19, 2016    (CH) .................................. 01683/16

(51) Int. Cl.
*A61N 1/04* (2006.01)
*A61B 5/00* (2006.01)
(Continued)

(52) U.S. Cl.
CPC ............ *A61N 1/0492* (2013.01); *A61B 5/259* (2021.01); *A61B 5/291* (2021.01); *A61B 5/6833* (2013.01);
(Continued)

(58) Field of Classification Search
CPC .... A61N 1/0492; A61N 1/048; A61N 1/0488; A61N 1/0476; A61B 5/259; A61B 5/291;
(Continued)

(56) References Cited

U.S. PATENT DOCUMENTS 116,197 A * 6/1871 Kidder ..................... A61N 1/04
607/150
3,505,993 A     4/1970 Lewes
(Continued)

FOREIGN PATENT DOCUMENTS

| EP | 0212096 | 3/1987 |
| EP | 2628502 | 8/2013 |
| WO | 2015187426 | 12/2015 |

OTHER PUBLICATIONS

Office Action (Notice of Allowance and Fees Due (PTOL-85)) dated Nov. 4, 2021 for U.S. Appl. No. 16/490,990 (pp. 1-6).
(Continued)

*Primary Examiner* — Eugene T Wu
(74) *Attorney, Agent, or Firm* — Graeser Associates International Inc; Dvorah Graeser

(57) ABSTRACT

The invention concerns an assembly (100) for delivering electrical currents to and/or sensing electrical signals from a skin portion of an individual. The assembly comprises an electrode (1) having an electrical conductive portion (2) with a surface for entering in contact with a skin portion (200) of the individual and an electrical insulating stratum (3) covering the electrical conductive portion (2). The assembly comprises a conductor assembly (40) having a connector assembly (4) with protuberances (8) for removably retaining the electrode and electrically connecting said electrical conductive portion (2) of the electrode to said monitoring and/or stimulating device. The protuberances have sharpened elements (8) for piercing the insulating stratum (3) and
(Continued)

engaging themselves inside the electrical conductive portion (2).

18 Claims, 4 Drawing Sheets

(51) Int. Cl.
    *A61B 5/259*     (2021.01)
    *A61B 5/291*     (2021.01)
    *A61B 5/257*     (2021.01)

(52) U.S. Cl.
    CPC ............ *A61N 1/048* (2013.01); *A61N 1/0488* (2013.01); *A61B 5/257* (2021.01); *A61B 2562/0209* (2013.01); *A61B 2562/227* (2013.01); *A61N 1/0476* (2013.01)

(58) Field of Classification Search
    CPC ................ A61B 5/6833; A61B 5/257; A61B 2562/0209; A61B 2562/227
    See application file for complete search history.

(56) References Cited

U.S. PATENT DOCUMENTS

| | | | | |
|---|---|---|---|---|
| 3,868,165 | A | * | 2/1975 | Gonser .................. H01R 11/24 439/410 |
| 4,126,126 | A | * | 11/1978 | Bare ........................ A61B 5/25 600/397 |
| 4,239,046 | A | | 12/1980 | Ong |
| 4,702,256 | A | * | 10/1987 | Robinson ............... A61B 5/274 403/111 |
| 4,768,514 | A | | 9/1988 | De Marzo |
| 5,285,781 | A | | 2/1994 | Brodard |
| 5,624,281 | A | * | 4/1997 | Christensson ......... A61B 5/274 439/729 |
| 6,701,189 | B2 | | 3/2004 | Fang |
| 2001/0000187 | A1 | | 4/2001 | Peckham |
| 2002/0188331 | A1 | | 12/2002 | Fang |
| 2008/0177168 | A1 | | 7/2008 | Callahan |
| 2008/0288020 | A1 | | 11/2008 | Einav |

OTHER PUBLICATIONS

Office Action (Notice of Allowance and Fees Due (PTOL-85)) dated Dec. 7, 2021 for U.S. Appl. No. 16/490,990 (pp. 1-2).

* cited by examiner

ELECTRODE AND CONNECTOR ASSEMBLIES FOR NON-INVASIVE TRANSCUTANEOUS ELECTRICAL STIMULATION AND BIOLOGICAL SIGNAL SENSING

FIELD OF THE INVENTION

The present invention concerns an electrode assembly for non-invasive transcutaneous electrical stimulation or biological signal sensing.

In particular, the invention concerns an assembly for delivering electrical currents to and sensing electrical signals from a skin portion of an individual, an electrode for entering in contact with the skin portion, and a conductor for operationally connecting the electrode to a monitoring or stimulating device.

DESCRIPTION OF RELATED ART

Medical and recreational electrode assemblies for non-invasive transcutaneous electrical stimulation or biological signal sensing are well known in the state of the art. The assemblies are meant to adhere to the patient skin to electrically connect it to external apparatus for electrical stimulation or biological signal monitoring, without harming or damaging the patient skin. Medical electrodes generally include an electrically-conductive substrate for interfacing with the skin, an electrically-insulating layer for protecting the electrode from unwanted contacts, and a conductive lead wire operatively connectable to external apparatus for stimulation or sensing. This lead wire is generally secured at one end to the conductive part of the electrode, and to a connector or plug to the other end, allowing electrical continuity with an external apparatus.

The electrical connection of such electrodes to an external device is generally established by plugging the electrode to a connector attached to a cable leading to the external device.

WO2016001393 A1 and US20110201913 describe medical electrodes connectable to external devices by snap connectors. However, the forces applied while connecting and disconnecting the electrode cannot be controlled due to the design of the snap mechanism itself. These forces may damage the electrode (e.g. the electrically-insulating layer that secures the snap component on the electrode side may be torn off, the small area of conductive substrate underneath the snap connector may be damaged by the excessive pressure applied) and compromise the proper attachment of the electrode to the skin, or make it completely unusable if the snap connector detaches from the electrode U.S. Pat. Nos. 4,239,046 and 4,848,351 disclose medical electrodes connectable to external devices by means of surfaces comprising conductive hooks and loops fasteners. An electrical contact is established by pressing together the two surfaces with cooperating hooks and loops, one attached to the top surface of the electrode and the other one to the conductive lead wire.

U.S. Pat. Nos. 4,112,941, 4,653,503, US20150303619, U.S. Pat. Nos. 9,050,451, and 4,067,342 disclose medical electrodes employing magnetic connectors for contacting the electrodes with external devices. An electrical connection is realized by lodging a magnetic connector in an electrical receptacle.

U.S. Pat. No. 5,168,875 describes an electrode being connectable to an external device by means of a connector pin insertable in predefined cavity of the electrode so as to make contact with the electrically-conductive substrate of the electrode. Once inserted, the connection is stabilized by fixing the outer part of the connector pin to the external surface of the electrode by means of an adhesive band to prevent retraction.

However, these electrodes suffer from several problems that limit their versatility, usability and sustainability.

First, most of these electrodes require one electrical conductive element on the disposable electrode for providing an electrical connection, such as a metallic plug, receptacle, pin, or magnet. The material used to manufacture the electrode connector constitutes valuable material which is trashed together with the rest of the electrode once the electrode is disposed, including metals or ferromagnetic components. As medical and recreational electrodes consumption is steadily growing, it would be desirable to use less material as possible on the disposable electrode.

Second, most of these electrodes are barely connectable to an external device with a single hand and make it cumbersome for a user alone to apply the electrode on his/her body without third party help, notably when the connection plugging requires a certain amount of force for ensuring a secure and stable connection.

Moreover, the design and the structure of most of these electrodes imply an important amount of force for connecting and disconnecting the electrodes so as an improper force may damage the electrode and/or compromise the proper attachment of the electrode to the skin. An excessive pressure can damage, notably, the electrically-insulating layer that secures the connection element on the electrode and the small area of conductive substrate underneath the connection element.

Another drawback of these electrodes is a connection requiring a proper alignment between the connection elements. The connection pairing increases the manipulation complexity and the time needed to correctly secure the electrode to an external device, like in the case of snap connectors.

BRIEF SUMMARY OF THE INVENTION

The aim of the invention is to provide an assembly for non-invasive transcutaneous electrical stimulation or biological signal sensing devoid of, or at least attenuating, the drawbacks of the known electrode assemblies.

In particular, an aim is to provide an assembly that is cheaper to manufacture and more ecologically sustainable by design.

Another aim is to provide an electrode assembly wherein the connector can be easily connected and disconnected with a single hand.

According to the invention, these aims are achieved by means of the assembly of claim 1, the connector assembly of claim 3 and the electrode of claim 14. Dependent claims describe particular embodiments of the invention.

The proposed solution provide an electrode assembly wherein the temporary and reversible connection between a disposable electrode and an external apparatus is realized through a connector providing stable electrical connection and mechanical fixing without requiring an interrelated, electrical conductive element on the surface of the electrode, such as a receptacle, a plugs, a velcro, a magnetic or snap connector.

The prosed solution provides thus an electrode assembly that is cheaper to manufacture and more ecologically sustainable by design, as the disposable electrode has a simplified structure and does not require any fastening means.

In one particular embodiment, the connector assembly comprises a portion configured to take the inserting (second) configuration, in response to an external force, for modifying the orientation of the sharpened elements from an inclined orientation to a perpendicular orientation with respect to the conducting portion of the electrode.

The proposed solution provides an electrical connection and disconnection of the electrode to an external device, wherein the connector can be easily connected and disconnected with a single hand, without the need to plug the connector to any specific electrode element, and without exerting forces that may shorten the electrode's lifetime.

Moreover, the proposed solution enables a simultaneously operational connection of multiple external devices to the same electrode assembly by means of a plurality of connectors attached to the same electrode assembly.

In one particular embodiment, the proposed solution provides an electrode assembly having a top, insulating surface of the electrode being self-healing so as to provide reparations, or at least attenuation, of damages caused by the connector assembly once removed.

In one particular embodiment, the electrical conductive portion of the electrode comprises a plurality of electrical conductive portions in electrical contact with a part of the skin portion of the electrode, each conductive portion being configured for substantially confining delivering or sensing electrical signals within the portion. Alternatively or complementarily, the electrical conductive portion of the electrode comprises one or more layers providing substantially monotonically-increasing electrically conductivity along a direction towards the skin portion.

This particular solution permits to tune the dimension and/or the position of the electrically-stimulated area on the skin without moving the electrode, but only by repositioning the connector assembly on the surface of the electrode, according to the needs of the user.

This particular solution permits to solve the problem affecting the medical and recreational practices consisting in the need of reposition the medical electrode on the skin of the user multiple times in order to place the electrode in the proper anatomical area, i.e. by successively removing and reattaching the electrode in another position on the skin of the patient/user. Being this process dependent on the anatomy of the user, it is complicated and time consuming. Furthermore, as the portion of the electrode in contact of the skin is generally adhesive, the user may experience discomfort or pain when an electrode is detached and reattached multiple times. Moreover, multiple repositioning causes the decline of the adhesiveness of electrode substrate, which may lead to an unwanted detachment during stimulation and forces the user to substitute the electrode with a new one.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
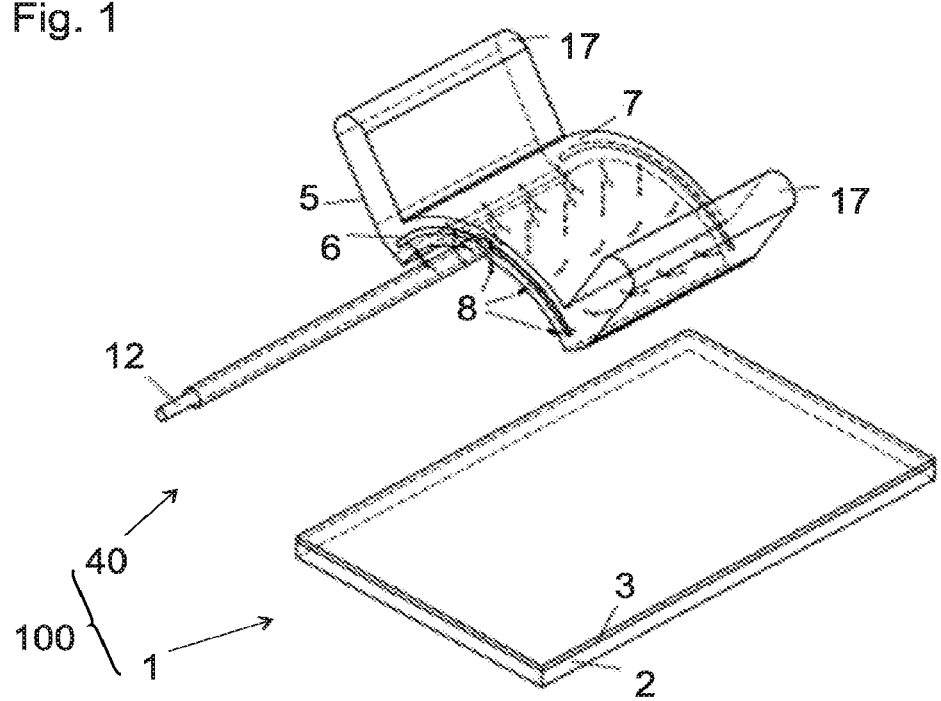
FIG. 1 shows a view of an assembly comprising a connector and an electrode assembly, according to the invention.
Figure 2:
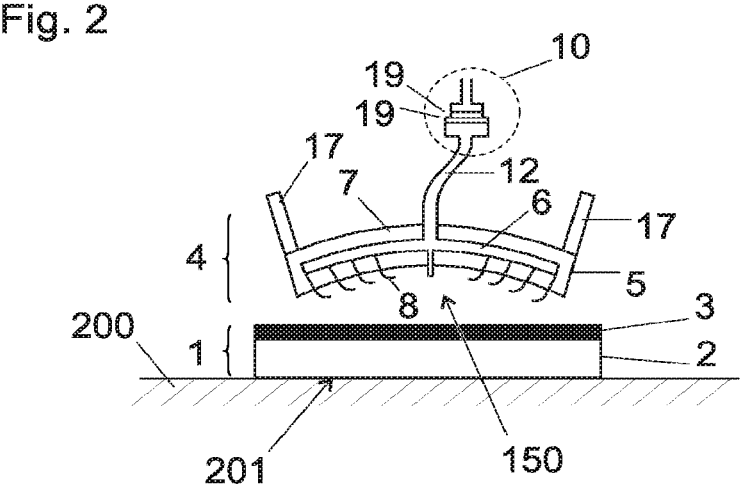
FIG. 2 shows a cross section of the assembly of FIG. 1.

FIGS. 1 and 2 show an assembly 100 for non-invasive transcutaneous electrical stimulation or biological signal sensing.

The assembly 100 is configured to deliver electrical currents to and/or to sense electrical signals from a skin portion 200 of an individual. The assembly 100 comprises an electrode 1 for entering in contact with the skin portion 201, and a conductor 40 for operationally connecting the electrode 1 to a monitoring or stimulating device (not illustrated).

The electrode 1 is a non-invasive transcutaneous electrode. The electrode is configured to deliver electrical currents to and/to sense electrical signals from the skin portion 200 of an individual by means of an electrical conductive portion 2 having a surface 201 for contacting the skin portion. Advantageously, the electrode comprises an insulating stratum 3 covering the electrical conductive portion 2, in order to prevent the user from undesired electrical contact during the procedure.

The insulating stratum 3 can be made of a single layer or film of a material, or can be composed by a plurality of layers, film or elements.

Advantageously, the insulating stratum 3 covers substantially the electrical conductive portion 2 so that the electrical conductive portion is devoid of exposed electrical conductive surfaces or elements, i.e. surfaces and element being directly contactable from outside the electrode when the electrode is operationally located on a skin portion. These embodiments prevent the user from undesired electrical contact during the procedure while protecting the electrical conductive portion from dirt and other damaging substances (notably liquids) that could damage the structure and/or the operability of the electrical conductive portion of the electrode.

The electrical insulating stratum 3 is further configured to permit a sharpened element to pierce it, while the conductive portion 2 is configured to receive and/or retain an electrical conductive element so as to provide an electrical contact with it.

The conductor assembly 40 of the assembly 100 is configured to operationally connect the electrode 1 to a monitoring and/or stimulating device, in particular to electrically connect the conductive portion of the electrode to the monitoring/stimulating device, and to retain the electrode and the conductor in a relative positioning by means of gripping means 8.

The conductor assembly 40 comprises a lead conductor 12 and a connector assembly 4 having gripping means 8. The lead conductor can take form of a lead wire or of a lead electrical band.

The gripping means comprise protuberances 8 extending from a surface 150 of the connector 4. The surface 150 can be advantageously configured to enter in contact with the electrode, for example with the electrical insulating stratum of the electrode.

The protuberances comprise at least one electrical conductive protuberance 8 (preferably a plurality of electrical conductive protuberances) for providing an electrical contact with the electrical conductive portion 2 of the electrode.

The protuberances comprise at least one retaining protuberance (preferably a plurality of retaining protuberances) for operationally retaining the electrode, i.e. for ensuring a mechanical adhesion of the electrode with the connector. The retaining protuberance can be made of a non-conductive material.

Advantageously, as illustrated in FIGS. 1 and 2, a same electrical conductive protuberance 8 can be configured to provide both an electrical contact with the electrical conductive portion 2 of the electrode and an operationally retaining of the electrode, i.e. configured to simultaneously operate as an electrical conductive protuberance and as a retaining protuberance.

In particular, the surface 150 can be a surface of a body 5 of the connector. The connector body 5 can comprise one electrically-insulating part 7 for providing easy and safe manipulation of the connector 4 and one electrical conductor 6 for connecting the electrical conductive protuberances 8 to the lead connector 12. The connector body can be either made in soft, deformable materials or rigid and not deformable materials.

Each conductive protuberance 8 has an electrical surface that is electrically connected to the lead conductor 12 by means of an electrical conductor 6 so as to permit electrical signal to be delivered to and/or sense from these protuberances. These protuberances are configured, once inserted in the electrode, to electrically connecting the electrical conductive portion 2 of the electrode to the monitoring and/or stimulating device. Advantageously, each conductive protuberance 8 is further configured to provide a mechanical adhesion (retention) of the electrode to the connector.

The protuberances 8 (gripping means) of the connector assembly 4 either are or comprise sharpened elements permitting them to penetrate (pierce) the electrode and to engage themselves inside the electrode 2, for providing an electrical contact and/or a retaining force between the conductor 12 of the conductor assembly 40 and the electrode 1.

The sharpened elements of the electrical conductive protuberances are configured to pierce (penetrate) the electrical conductive portion 2 of the electrode 1. Advantageously the sharpened elements of the electrical conductive protuberances are further configured to pierce an insulating stratum 3 eventually covering the electrical conductive portion 2 of the electrode 1 for preventing undesired electrical contact during delivering electrical currents to and/or sensing electrical signals.

The sharpened elements of the retaining protuberances are configured to insert themselves within a portion of the electrode so as to provide a retaining force for retaining the electrode and the connector together, notably by piercing (penetrating) the insulating stratum 3 and/or the electrical conductive portion 2.

The (electrical conductive and/or retaining) protuberances 8 (gripping means) should be sufficiently stiff in bending and in tension in order not to break due to the forces involved in self-gripping, e.g. penetration into the electrically-insulating stratum 3 of the electrode 1.

The (electrical conductive and/or retaining) protuberance can take different forms and dimension, such as an elongated element having, for example, a substantially circular, square, triangular, or polygonal section. The conductive protuberance can also take a form of a stocky element, such as a chunk, or a blade-, a wall- or undulating-shaped piece.

The conductive protuberance can entirely be made of one or more conductive materials. Alternatively, the conductive protuberance can have a structure made of an electrical non- or less-conductive material providing the necessary stiff in bending and in tension, the conductive protuberance further comprising electrical conductive surfaces in electrical connection with the lead conductor 12.

The conductive protuberance can be made of, or comprise, metal (e.g. steel, aluminium, silver, gold) or conductive polymers, e.g. carbon nanotubes (CNTs) embedded polymers or carbon black polymer composites, highly conductive poly(methyl methacrylate) (PMMA)-reduced graphene oxide composite or conductive polystyrene (PS) or polymers coated with metals (e.g. ABS, PEEK, PS metallized with gold or platinum by means of physical vapor deposition (PVD), having those polymers a tensile modulus comprised between 0.1 and 700 GPa but preferably between 1 and 300 GPa.

The conductive protuberances 8 of the exemplary embodiment of FIGS. 1 and 2 have form of conductive elongated protuberances, e.g. made of conductive stems. The conductive protuberance 8 are secured on the connector assembly 4 in electrical connection with the external device through the electrically conductor 6 and the lead conductor 12. The conductive protuberances are dimensioned so that they can penetrate the whole electrically-insulating stratum of the electrode but not the complete thickness of the electrode: therefore, when the connector 4 is positioned anywhere on the surface of the electrode, the gripping means 8 can mechanically and electrically fasten the electrically-conductive portion 2 of the electrode 1 with the external device in a temporary and reversible manner.

FIG. 6 shows several examples of conductive and/or retaining protuberances 8 of the gripping means. The protuberance 8 comprises an elongated body 80 and a sharpened end 11.

Figure 6A:
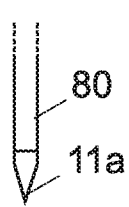
FIGS. 6A-6D show exemplary embodiments of protuberances of the connector assembly, according to the invention.
Figure 6B:
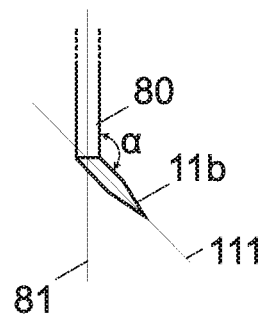
Figure 6C:
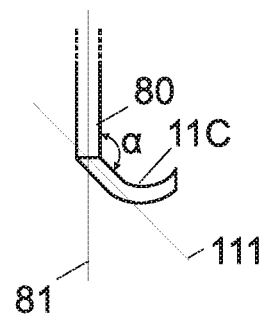

In most embodiments, the sharpened end is the free end 11 of the gripping means 8, notably the free end of the elongated body 80. The sharpened end can be oriented either in the same direction of the longitudinal axis 81 of the elongated body 80, as shown in FIG. 6A, or can form an angle a with respect to it, as shown in FIGS. 6B and 6C.

The free end 11 can form a permanent angle a in a range from 90° to 180°. Preferably, the angle a is in a range of 135°+/−15°.

The sharpened end can have an elongated portion 111 with a longitudinal axis being inclined with respect to a longitudinal axis 81 of the elongated body.

The sharpened end can be conical-shaped 11a, 11b, curved 11c, hook-shaped 11d or having a shaped profile facilitating the penetration into the electrically-insulating stratum 3 of the electrode 1.

In some embodiments, the (conductive and/or retaining) protuberance comprises one or more substantially radially extending element 18 for providing retaining force once the protuberance is located inside the electrode, in particular inside the electrical conductive portion. The extending element 18 can have different shapes, e.g. bristles, hooks, rods, wedge shaped barbs, scales. The extending element can be inclined to the protuberance so as to offer low resistance to penetration into and high resistance to withdrawal from the electrically-insulating stratum of the electrode. The extending element can have dimensions comparable to the diameter of the elongated body of the conductive protuberance.

Advantageously, the radially extending element(s) 18 are electrical conductive element providing an electrical contact between the electrical conductive portion of the electrode and the lead conductor.

Figure 6D:
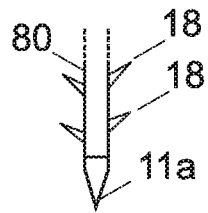

In FIG. 6D is illustrated an exemplary embodiment of a conductive protuberance comprises a plurality of radially extending element 18. In this embodiment, the radially extending elements 18 are retaining nibs 18 radiating from the elongated body 80. These nibs have a form of bristles, advantageously of shaped barbs. The nibs are (backwardly) inclined to offer low resistance to penetration into and high resistance to withdrawal from the electrically-insulating portion of the electrode. Such retaining nibs can have dimensions comparable to the diameter of the body portion 80.

In a preferred embodiment of the connector 4, the gripping means (conductive and/or retaining protuberances) 8 are in a range in length from about 500 µm to about 5000 µm but preferably between 1000 µm and 3000 µm. The diameter and/or section of said gripping means (conductive and/or retaining protuberances) 8 are in a range between about 50 µm and about 1000 µm, preferably between about 100 µm and about 300 µm. Preferably the gripping means 8 are made of steel. Preferably the gripping means 8 have sharpened free end 11 that permanently form an angle a comprised preferably between 0 and 90° with respect to the longitudinal axis of the conductive protuberance and/or elongated body.

The gripping means (conductive and/or retaining protuberances) may be homogeneously distributed on the surface 150 of the connector, with a density preferably in a range from 1 gripping means per square centimeter to 40 gripping means per square centimeter.

Alternatively or complementarily, the gripping means (conductive and/or retaining protuberances) may also be not homogeneously distributed. For example, they may be present with an higher density on the two symmetric portions of the connector body 5 far from the vertical plane (i.e. the plane perpendicular to the frontal plane and the surface of the connector body 5 intended to be in contact with the electrode 1, as shown in FIG. 1) of the connector 4, and have a lower density closer to the vertical plane.

As shown in FIGS. 1 and 2, the self-gripping action of the connector 4 can be enabled by the shape of the free ends 11 of the gripping means (electrical conductive and/or retaining protuberances) 8 and/or the orientation of said gripping means 8. In the preferred embodiment of the connector 4, the self-gripping action is enabled by a variable orientation of the gripping means 8, being said gripping means 8 firmly secured to a reconfigurable connector body 5. Specifically, by applying a mechanical force to (a given portion 17 of) the self-gripping connector 4, said gripping means 8 can be oriented to offer little resistance to penetration into the electrically-insulating portion 3 of the electrode 1. By releasing said mechanical force, the gripping means 8 return to the original orientation to offer greater resistance to detachment.

FIG. 3 shows a cross-section of an embodiment of the electrode 1 and the self-gripping connector 4 in different configurations. FIG. 3A shows the connector 4 in a resting, electrode-detached configuration. FIG. 3B shows the connector 4 in a prepared-for-attachment configuration. FIG. 3C shows the connector 4 in an electrode-attached configuration. FIG. 3D shows the connector 4 in a prepared-for-detachment configuration.

Figure 3A:
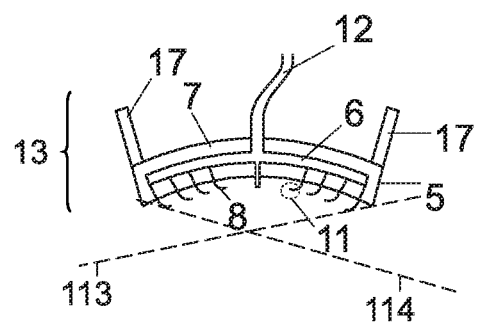
FIGS. 3A-3D illustrate the connector assembly of FIG. 1 evolving between a resting position and a fixing position for connecting and disconnecting the electrode assembly.

FIG. 3A shows an embodiment of the connector 4 wherein the connector body 5 is in a resting, electrode-detached configuration 13. The gripping means 8 located on the side of the connector body 5 are bent, e.g. by means of an inclined sharpened end 11. Moreover, in this configuration, the inclined orientation 113, 114 of the sharpened end 11 make the gripping means unable to harm the skin of a patent following of an involuntary contact with the connector.

Figure 3B:
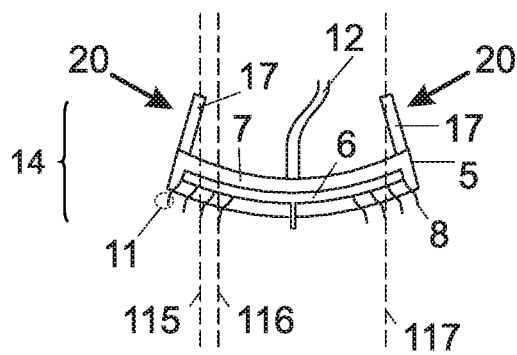

FIG. 3B shows the connector body 5 in a prepared-for-attachment configuration 14. The free ends 11 of the gripping means 8 (sharpened end of the electrical conductive and/or retaining protuberances) are oriented 115, 116, 117 such that they can easily penetrate the electrically-insulating stratum 3 of the electrode. For example, the free ends of the gripping means 8 are close to be perpendicular to the surface of the electrically-insulating stratum of the electrode. The transition between electrode-detached configuration 13 and prepared-for-attachment configuration 14 can be caused by the application of a mechanical force, being this force applied, for example, by the fingers of the user onto the manipulating means 17 of the connector body 5. In the illustrated embodiment, this applied force results into an elastic deformation of the connector body 5, the connector body 5 being an elastically deformable body.

In another embodiment, the applied force can result into a transition of the connector body 5 from one state (configuration) of minimal energy to another, the connector body 5 being a multi-stable system (i.e. with multiple stable equilibrium points).

In order to facilitate the connection and disconnection of the connector assembly 4 with the electrode 1 when the electrode is fixed on a skin portion of an individual, the connector assembly can thus comprise a portion 5 (notably of the connector body 5) capable to take a first configuration (resting configuration) and a second configuration (inserting configuration) in response to a force so as to modify a relative orientation of the sharpened elements 8 for permitting them to pierce the electrode, in particular the electrical insulating stratum and/or the electrical conductive portion of the electrode. The body connector can comprise, or even constitute, this portion.

Advantageously, the portion is a resilient portion 5 deformable from the rest configuration to the inserting configuration in response to a force so as to modify the relative orientation of the protuberances 8, i.e. the sharpened elements 8.

Alternatively, the portion is a moveable portion having two or more distinct sub-portions or surfaces relatively moveable (e.g. pivotally) the one with respect to the other so as to modify the relative orientation of the protuberances 8, i.e. the sharpened elements 8.

Advantageously, the moveable portion is moveable in response to a pair of opposed forces applied to a first and second application points of the connector body, advantageously in response of a force applied by fingers of the individual.

In the inserting configuration, the protuberances 8, i.e. the sharpened elements (e.g. the elongated bodies 80 and/or the sharpened ends 11), are advantageously oriented substantially along parallel directions so as to permit the sharpened element to pierce the electrical insulating stratum and to insert themselves inside the electrical conductive portion of the electrode when the electrode is fixed on a skin portion of an individual. As illustrated in the exemplary embodiments of FIGS. 3B and 3D, the (resilient/moveable) portion 5 permits to orientate the protuberances 8 (i.e. sharpened elements) in directions 115, 116, 117 that are locally perpendicular to surface portions of the electrode (e.g. the electrical insulating stratum 3) once it was fixed to a skin portion.

Figure 3C:
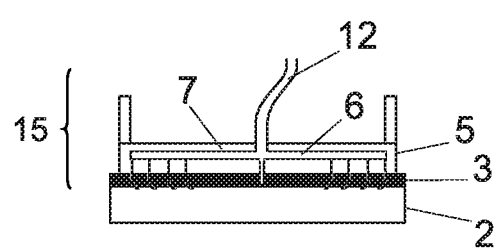

As illustrated in FIG. 3A, in the rest configuration, the protuberances 8, i.e. the sharpened elements (e.g. the elongated bodies 80 and/or the sharpened ends 11), are oriented substantially along axes 113, 114 that are relatively inclined among them. This provides, once the sharpened element being inserted in the electrode along substantially parallel directions, a retaining force between the electrode 1 and the connector assembly 4, as illustrated in FIG. 3C.

FIGS. 2, 3A-3D show embodiments where the connector assembly comprises a resilient portion, notably of the connector body, that is deformable from a rest configuration to a second configuration in response to an external force 20 so as to modify the orientation of at least part of the protuberances 8 (i.e. sharpened elements) for piercing the insulating stratum. In the second configuration, the protuberances 8 (i.e. sharpened elements) are essentially perpendicular to a surface of the electrode, notably to a surface of the electrical insulating stratum and/or of the electrical conducting portion of the electrode, while, in the rest configuration, the protuberances 8 (i.e. the sharpened elements) are inclined relative to these surface of the electrode. This surface is generally flat when the electrode is attached to a skin portion, in particular the surface 201 of the electrode destined to enter in contact with a skin portion or an external surface of the electrical insulating stratum.

The resilient portion is deformable in response to a pair of opposed forces 20 applied to a first and second application points 17, advantageously in response to a force applied by fingers of the individual. The application points are, for examples, manipulating means taking form of manipulating surfaces of the connector body 5 or dedicated elements 17 connected to the connector body 5.

The resilient portion provides both connecting and disconnecting of the electrode by a single hand, notably by means of two fingers of them.

To fasten the connector 4 to the electrode 1, the connector in the prepared-for-attachment configuration 14 is pressed against the surface of the electrically-insulating portion 3 of the electrode with sufficient force to cause the properly oriented free ends 11 of the gripping means to penetrate the opposing surface and lodge therein.

The gripping means 8 are arranged in a matrix. The gripping means 8 comprise electrical conductive protuberances in the row along the vertical plane of the connector 4. These electrical conductive protuberances are straight, being always perpendicular to the surface of the electrode 1 regardless the configuration of the connector 4. They contribute to electrical fastening but not to the mechanical one (i.e. their presence does not impact on the maximum pulling force that the connector 5 can withstand before detaching). The gripping means 8 further comprise retaining protuberances positioned on the two sides of the vertical plane. In the embodiments of FIGS. 2, 3A-3D, these retaining protuberances progressively increase in curvature (towards the free extremity of the free end 11 with respect to the longitudinal axis 81 of the protuberances, e.g. the free end 11 can be arc-shaped ends) providing for increasing self-gripping force as the gripping elements penetrate the electrically-insulating portion 3 of the electrode. These retaining protuberances can be even electrical conductive protuberances, i.e. providing electrical contact between the electrical conductive portion of the electrode and the lead conductor.

FIG. 3C shows the connector body 5 in an electrode-attached configuration 15. The free ends 11 of the gripping means 8 are oriented such that they resist withdrawal of said gripping means 8 from the attached insulating part 3: for example, the gripping means 8 are inclined towards the center axis of the self-gripping connector 4. The transition between the prepared-for-attachment configuration 14 to the electrode-attached configuration 15 can be caused, for example, by the removal of a mechanical force, previously applied to the connector body 5 to elastically deform it, being the connector body 5 an elastically deformable body. This action can result into the elastic return of the connector body 5 to a different configuration. In another embodiment, the transition between the prepared-for-attachment configuration 14 to the electrode-attached configuration 15 can be caused by a transition of the connector body 5 from one state of minimal energy to another, being the connector body 5 a multi-stable system.

Figure 3D:
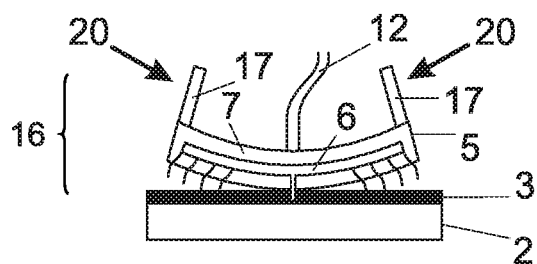

FIG. 3D shows the connector body 5 in a prepared-for-detachment configuration 16. The free ends 11 of the gripping means 8 are oriented such that they can easily withdraw from the electrically-insulating portion 3 of the electrode 1. For example, the gripping means 8 are close to be perpendicular to the surface of the electrically-insulating portion 3. Like the abovementioned transition between the electrode-detached configuration 13 and the prepared-for-attachment configuration 14, the transition between the electrode-attached configuration 15 and the prepared-for-detachment configuration can be caused by either elastic deformation of an elastically deformable connector body 5 or transition from one state of minimal energy to another in case of multi-stable connector body 5.

The illustrated configurations of the connector body 5 show the prepared-for-detachment configuration 16 that substantially correspond to the prepared-for-attachment configuration 14. This is not an essential feature, as in other embodiments of the connector body, the prepared-for-detachment configuration 16 can differ from the prepared-for-attachment configuration 14.

The mechanical fastening, i.e. the resistance to forces needed to penetrate and to disengage the electrode, of the self-gripping connector 4 is determined by the stiffness, the number and distribution of the gripping means 8. For example, the number and the distribution of the gripping means 8 should be enough for the connector in the electrode-attached configuration 15 to withstand pulling forces at least up to 20N, like those measured while unplugging a standard cable connector from an Axelgaard PALS® electrode (traction test realized with a MTS LSB.102 force transducer, with a sensitivity of 2.044 mV/V, sampling rate 10 Hz, 1 mm/s traction speed). It has been found that a connector 5 with gripping means 8 shaped as hooks (0.25 mm diameter, protruding 0.5 mm from the flat connector body) and arranged in two rows positioned on the two sides of the vertical plane of the connector (5 mm far from the vertical plane), made of steel, can withstand comparable pulling forces if the number of said hooks is at least 6 hooks.

FIG. 4 shows other embodiments of the connector 4.

Figure 4A:
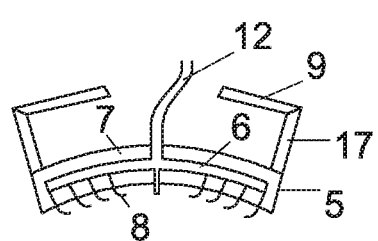
FIG. 4A-C shows others exemplary embodiments of the connector assembly, according to the invention.

In particular FIG. 4A shows an embodiment of the connector 4 wherein blocking means 9 are added to the connector body 5 to prevent the connector 4 to deform further than an allowed configuration.

FIG. 4A shows the connector 4 having an elastically deformable connector body 5 and manipulating means 17 wherein the mechanical force for reconfiguration can be applied. The gripping means 8 are shaped as hooks. This embodiment of the connector comprises blocking means 9 that limit the mechanical deformation of the connector body 5 in the prepared-for-attachment 14 or the prepared-for-detachment 16 configurations. For example, the blocking means 9 can be protrusions of the manipulating means 17 that are projected towards the vertical plane of the connector. When a mechanical force is applied by the finger of the user on the manipulating means 17, the connector body 5 deforms until the two blocking means 9 touch each other along the vertical plane of the connector. This blocking means 9 thus optimally constrain the orientation of the free ends 11 of the gripping means 8 to allow an easy penetration/removal of/from the electrically-insulating portion 3 of the electrode 1 by the gripping means 8.

Figure 4B:
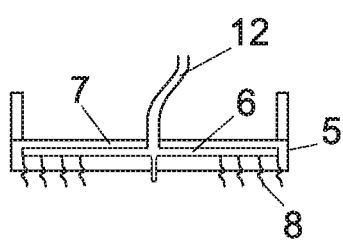

FIG. 4B shows an embodiment of the connector 4 wherein the gripping means 8 have barbed-wire like structures to improve the adhesion to the electrode 1.

FIG. 4B shows another embodiment, wherein the self-gripping action is given by the shape of the gripping means 8, being said gripping means 8 shaped as stems with retaining nibs 18 and perpendicularly oriented with respect to the surface of the electrode 1. Such gripping means 8 can easily penetrate the opposing surface of the electrically-insulating portion 3 of the electrode and lodge therein; when pulled apart, they behave like hooks and resist to withdrawal. The electrically-insulating stratum 3 of the electrode can self heal after the withdrawal of the gripping means 8 due to the self healing material of which it is made of. In this embodiment, the connector can have one single configuration, corresponding to the resting, electrode-detached configuration 13, being the self-gripping action of the connector (4) enabled just by the shape of said gripping means (8).

Figure 4C:
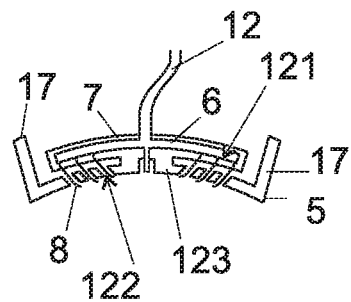

FIG. 4C shows another embodiment wherein the self-gripping action is enabled by a variable orientation and a variable exposition of the gripping means 8. For example, the gripping means 8 in a resting configuration are not exposed, being said gripping means retracted inside holes 122 into the connector body 5 and firmly secured to a flat protrusion 121 on the top surface of said base 123 of the connector body 5. By applying a mechanical force to the manipulating means 17, the deformation of the base 123 of the connector body 5 against the flat protrusion 121 forces the gripping means 8 to slide inside the holes 122 and to protrude out the base 123 of the connector body 5 on the electrode-side. Moreover, said deformation of the base 123 of the connector body 5 also orient the gripping means 8 to offer little resistance to penetration into the electrically-insulating portion 3 of the electrode 1.

In another embodiment, the self-gripping action is enabled by a reconfigurable orientation of the free end 11 of the gripping means 8, said free ends 11 being able to re-orient due to active means (e.g. chemicals, heating as disclosed in U.S. Pat. No. 3,494,006 as a fabrication step). For example, the gripping means in a resting configuration can be straight stems oriented perpendicular to the surface of the electrically-insulating portion 3 of the electrode 1 to decrease the resistance to penetration, wherein the free ends 11 are aligned with the vertical axis of the gripping mean body. After penetration, the joule heating due to the passage of stimulating current triggers a change of shape/orientation of free ends 11 or of the whole gripping mean 8, being the gripping means 8 made of shape memory alloy or composed by two metals (e.g. steel and copper) which expand at different rates when heated. In this second configuration (e.g. stem with a free end curved like an hook), the gripping means 8 offers an increased resistance to withdrawal. At the end of the stimulation, the gripping means return in resting configuration and can be easily withdrawn from the electrode 1.

A curved surface of the connector body 5 supporting the gripping means (electrical conductive protuberances), e.g. as shown in FIG. 4A, has two main advantages over a flat one, e.g. embodiment shown in FIG. 4B. Firstly, in the resting, electrode-detached configuration 13, the free ends 11 of the gripping means 8 are not exposed to user contact. Secondly, being the connector body 5 an elastically deformable body, the transition between the prepared-for-attachment configuration 14 to the electrode-attached configuration 15 can be driven by a strong elastic return. This elastic return does not occur completely due to the mismatch between the mainly flat electrode surface and bent connector surface, this meaning that the connector body 5 in the electrode-attached configuration 15 still experiences an internal stress which increases the self-gripping action.

The protuberances (i.e. gripping means) can be made via molding, for example as disclosed in EP1749456 A1. If present, the radially extending elements (e.g. retaining nibs) can be integral with the protuberances and therefore made of the same material; they can also be simply attached to the protuberances (e.g. tight fit, adhesive) and made of a different material.

Alternatively, once the gripping means being manufactured, they can be operationally fixed on the body connector by projection, e.g. via high pressure injection such as air jet, so as they can penetrate the electrically-insulating part 7 of the connector body 5 and reach the electrical connector 6 of the connector body 5, being this electrical connector 6 made of penetrable and deformable material.

The electrical conductor 6 of the connector body 5 can be made of conductive deformable material such as conductive elastomer, conductive fabric (e.g. Medtex Balingen by Scieldex), wire mesh, liquid metallic alloy at room temperature (e.g. Eutectic Gallium Indium). Notably in case of a rigid body connector, it can be made of conductive rigid material such as metal (e.g. steel, aluminium, copper) or any rigid conductive polymers composites (e.g. carbon nanotubes (CNTs) or carbon black polymer composites, highly conductive poly(methyl methacrylate) (PMMA)-reduced graphene oxide composite or conductive polystyrene (PS)), shaped in structures with low bending stiffness at least in one plane perpendicular to the surface of the connector body 5 intended to be in contact with the electrode 1 (e.g. the frontal plane, as shown in FIG. 1).

In a particular embodiment, the gripping means 8 of the present invention can be directly part of the electrically-conductive portion or conductor 6 of the connector body. For example, the electrically-conductive portion or conductor 6 of the connector body 5 and the electrical conductive protuberances of the gripping means 8 can be formed from the same conductive material by injection molding, being the electrically-conductive part or conductor 6 shaped as a structure (e.g. serpentine, thin metal sheet) with low bending stiffness in a plane perpendicular to the surface of the connector body 5 to allow the deformation of the connector body 5. If the electrically-conductive part or conductor 6 is shaped as a structure with high bending stiffness in a plane perpendicular to the surface of the connector body 5, the connector body can still include deformable portions that allow a change in configuration of the connector The electrically-insulating part 7 of the connector body 5 partially or completely encapsulates the electrically-conductive part 6 and it can comprise protruding manipulating means 17 to provide an easy and safe manipulation of the connector 4 by the user. The electrically-insulating part 7 of the connector body 5 can be made of insulating, inherently deformable material, such as NinjaFlex® from NinjaTek or Estane® (series E, T and 58000, from Lubrizol) or any other kind of thermoplastic elastomer (TPE) suited for injection molding, extrusion molding or 3D printing and having a tensile modulus comprised between 0.1 and 100 MPa but preferably between 1 and 15 MPa. Alternatively, the electrically-insulating part 7 of the connector body 5 can be made of stiffer insulating polymers (e.g. ABS, PS, PE) arranged in a shape that allows the deformation of the connector body 5.

In some embodiments, the electrically-insulating part 7 of the connector body 5 can also comprise several materials with different stiffnesses, either molded sequentially or assembled (e.g. manipulating means 17 made of ABS assembled on elastomeric electrically-insulating part 7 of the connector body 5). For example, this allows building connectors with stiff manipulating means but still including deformable parts.

In a preferred embodiment of the connector 4, shown in FIG. 1, the connector body 5 is shaped as a curved rectangular plate with lateral protrusions, being these protrusions the manipulating means 17 to facilitate the manipulation of the connector 4 by the user. The curved rectangular plate is deformable. The thickness of said curved rectangular plate of the connector body 5 may range between about 0.5 mm and about 5 mm, preferably between about 1 mm and about 2 mm. The length of said connector body 5 may range between about 5 mm and about 100 mm, preferably between about 10 mm and about 20 mm. The width of said connector body 5 may range between about 5 mm and about 100 mm, preferably between about 10 mm and about 20 mm. The manipulating means 17 form an angle with respect to the vertical axis of the connector 4 ranging between 0 and +/−80 degrees, preferably between 20 and 45 degrees (positive values for angles towards the external side of the connector 4). Their length preferably ranges between 5 and 10 mm.

FIGS. 1 and 2 show an exemplary embodiment of the electrode 1. The surface 201 of the illustrated electrodes is a flexible surface, essentially flat surface, so to provide an ideal contact with a skin portion of an individual. Preferably said surface has an area of at least 1 cm$^2$.

In order to allow the electrical conductive protuberances to pierce the electrical insulating stratum, this stratum can made of, or comprising: a continuous foam backing sheet, an electrical nonconductive fabric layer, or a polymeric layer or coating, such as a polyethylene layer or coating.

The thickness of the electrical insulating stratum 3 of the electrode 1 is preferably in a range from 50 μm to 500 μm, preferably in a range from 100 μm to 300 μm, so as to provide an optimal penetration of the electrical conductive protuberances.

The electrically-insulating portion 3 of the illustrated electrode can comprise a deformable and penetrable polymeric film such as polyethylene film (as disclosed in U.S. Pat. No. 4,391,278 A), a continuous foam backing sheet without any openings (as described in US20080082153 A1) or a non-conductive fabric layer (as disclosed in U.S. Pat. No. 4,243,052 A). Such an electrically-insulating portion 3 of the electrode (1) can be held against the electrically-conductive portion 2 of the electrode (1) by e.g. means of a pressure sensitive adhesive (as suggested in U.S. Pat. No. 4,722,354 A), by curing them together or by knitting them together on top of each other.

Advantageously, the electrical insulating stratum 3 can comprise a resilient material having an ability to repair damages of the insulating stratum or at least to close or reduces holes of the insulating stratum caused by punctures. This embodiment provides self-repairing that could preserve the functionality of the electrode and the insulating functionality of the electrical insulating stratum in case of a repositioning of the electrical conductive protuberances on the electrode.

In particular, the electrically-insulating portion 3 of the electrode 1 can be made of flexible penetrable self-healing material (for example hindered urea bonds containing polymers, as described by Ying et al. (2014), Nature Communications, 5:3218) that can self-repair in case of puncture with or without the need of an external stimulus (e.g. light, temperature change).

The thickness of the electrical conductive portion is preferably in a range from 100 μm to 4000 μm, preferably in a range from 800 μm to 1200 μm, so as to provide an optimal retaining and electrical contact with the electrical conductive protuberances of the connector.

The electrical conductive portion can comprise an adhesive material for resiliently fixing the electrode to a skin portion, preferably the electrical conductive portion being made of an electrical conductive adhesive material.

In some embodiments, the electrically-conductive portion 2 of the electrode 1 can be composed of a single layer of adhesive and electrically-conductive material, with optimal electrical conductivity in the directions perpendicular and parallel to the skin.

Alternatively, the electrically-conductive portion 2 of the electrode 1 can also be composed of one layer of adhesive material which conducts preferentially along the direction perpendicular to the skin and a second layer of material which conducts preferentially along directions parallel to the skin, being this second layer attached to the first layer and to the electrically-insulating portion 3. The first layer, that is in contact to the skin, can be in the form of a hydrogel able to absorb and retain significant amounts of water (e.g. as the commercial available Axelgaard AG2540 Fastening gel), with a thickness between 0.2 and 5 mm and an electrical conductivity between 0.001 and $10^7$ S/m. The second layer can be in the form of either hydrogel, as for example disclosed in Ahadian et al. (2014), Scientific Reports, 4:4271, in the form of a conductive mesh/fabric as disclosed in U.S. Pat. No. 6,153,124 A or WO2014139825 A2, or in the form of a conductive composite film (e.g. silver grid patterns printed on carbon film in Axelgaard Ultrastim® electrodes), being this second layer preferably characterized by an electrical conductivity between 0.1 and 1000 S/m.

The electrical conductive portion can comprise a plurality of electrical conductive portions, each conductive portion being in contact with a distinct skin portion and being configured for substantially confining the deliver or sensing of electrical signals within the portion.

Alternatively or complementarily, the electrical conductive portion 2 comprises one or more layers 23, 24, 25 providing substantially monotonically-increasing electrically conductivity; the most conductive surface of said one or more layers being in proximity of the surface 201 for contacting the skin portion of the individual.

Figure 5:
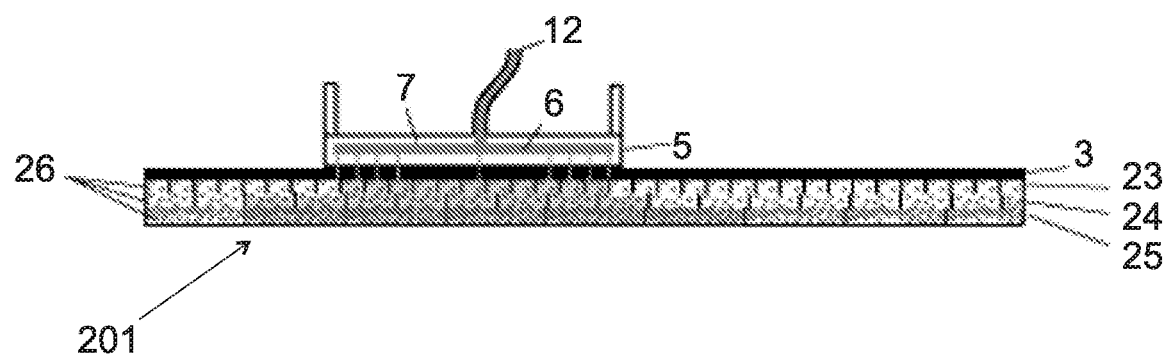
FIG. 5 illustrates a particular embodiment of the electrode assembly, according to the invention.

FIG. 5 shows an electrode composed of several conductive layers 23,24,25, composed of independent islands 26 (i.e. conductive electrical portions that are electrically-insulated from other islands, i.e. conductive portions, of the same layer) so as, when connected by electrical conductive protuberance, only a fraction of the islands conducts sufficient charge so as to selectively stimulate an underlying region of the skin portion.

The exemplary embodiments of the electrode of FIG. 5 comprises an electrically-insulating stratum 3 and an electrically-conductive portion 2, wherein the electrically-conductive portion 2 is made, for example, of three layers. The proximal layer 23 is attached to the electrically-insulating stratum 3 of the electrode 1. The distal layer 25 is in contact with a skin portion, being its inherent adhesiveness or an additional conductive adhesive used for adhering the electrode to the skin. A number of intermediate layers 24 are attached between the proximal layer 23 and the distal layer 25. Each layer of the electrically-conductive portion 2 is composed of a plurality of conductive islands 26. Said conductive islands 26 are not electrically connected to the neighbouring islands on the same layer. However, the conductive islands 26 are electrically connected to the neighbouring islands on the layers above and below, i.e. the conductive islands 26 of the intermediate layer 24 are electrically connected to the neighbour conductive islands 26 of the proximal layer 23 and distal layer 24.

The surface of the conductive islands 26 parallel to the electrically-insulating stratum 3 is defined the transversal surface.

In the exemplary embodiments of the electrode of FIG. 5, the transversal surface of the proximal layer 23 is smaller than the transversal surface of the conductive islands 26 of the distal layer 25. The transversal surface of the conductive islands 26 of the intermediate layers 24 increases in size as the layers are closer to the skin, i.e. the transversal surface of the conductive islands 26 of the proximal layer 23 is smaller than the transversal surface of the conductive islands 26 of the distal layer 25. The surface area of the conductive islands 26 of the proximal layer 23 measures from 2 to 4 mm$^2$. The conductive islands of the intermediate layer 24 are 4 times larger in area than the conductive islands of the proximal layer 25 so that the top surface of each conductive islands 26 of the intermediate layer 24 is in contact with four islands of the proximal layer 25. The size of the conductive islands 26 of the distal layer 25 thus depends on the number of intermediate layers 24. The total thickness of the electrode should not go above 5 mm.

The conductive islands 26 belonging to the same layer can have the same electrical conductivity, while the conductive islands 26 belonging to the different layers can have different electrical conductivities. Advantageously, the electrical conductivity within the conductive islands 26 increases as the layers are closer to the skin, i.e. the conductive islands 26 belonging to the distal layer 25 are more conductive than those of the proximal layer 23. This arrangement provides that electrical stimulation and sensing is directed substantially perpendicular with respect to the skin portion.

When the gripping means 8 of the connector 4 pierce the electrically-insulating portion 3 of the electrode 1, said gripping means 8 contact a number of conductive islands 26 belonging to the proximal layer 23. The number of contact will depend on the number of gripping means 8 of the connector as well as their density and the size of the conductive islands 26 of the proximal layer 23. The current injected by the connector 4 flows from the proximal layer 23 and spreads from one intermediate layer 24 to another by the contact of the conductive islands between each intermediate layer 24 and finally reaches the distal layer 25. As the conductive islands 26 are increasing in size, the current spreads in a conical shape through the electrode 1.

In some particular embodiments, the conductive islands 26 have transversal surface with a regular shape, e.g. circle, rectangle, square, pentagon, etc. The shape can be homogeneous throughout the same layer. In some particular embodiments, different layers have different transversal shapes or even heterogeneous shapes within the same layer.

These embodiments provide an electrode assembly wherein the electrically-stimulated area on the skin can be tuned in size and position without moving the electrode, but only repositioning the connector, according to the needs of the user.

This particular solution permit to solve the problem affecting the medical and recreational practices consisting in the need of reposition the electrode on the skin of the user multiple times in order to place the electrode in the proper anatomical area, i.e. the electrode, once applied, is removed and then reattached in another position. Being this process dependent on the anatomy of the user, it is complicated and time consuming. Furthermore, as the portion of the electrode in contact of the skin is generally adhesive, the user may experience discomfort or pain when an electrode is detached and reattached multiple times. Multiple repositioning causes the decline of the adhesiveness of electrode substrate, which may lead to an unwanted detachment during stimulation and forces the user to substitute the electrode with a new one.

The conductor assembly 40 can comprise a safety release mechanism 10. This safety means 10 disconnect from the electrically-conductive lead wire 12 when a pulling force that can damage the attached self-gripping connector 4 is applied on the electrically-conductive lead connector or wire 12. Typically, such pulling force should not exceed the gripping force of the standard cable connector, namely 20N as mentioned above. Said safety means 10 can be conventional cable connectors like the one disclosed in U.S. Pat. No. 6,418,347 B1, or magnetic type connectors using a magnet (19) to secure the connection as disclosed in U.S. Pat. No. 7,311,526 B2, or a velcro type connector as disclosed in U.S. Pat. No. 4,239,046.

FIG. 7 shows the experimental setup used to validate the efficacy and the efficiency of the connector of the present invention.

Figure 7A:
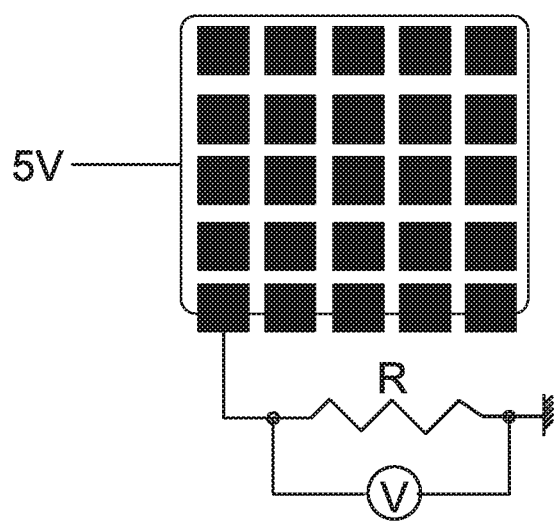
FIG. 7 shows an experimental setup used to validate the embodiments of the present invention.
Figure 7B:
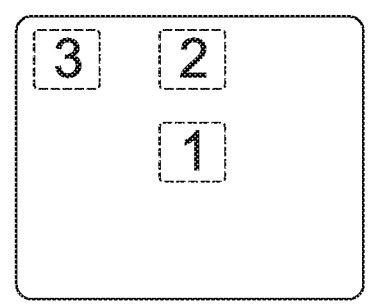

FIG. 7A shows the experimental apparatus used to characterize the voltage readout on different areas of an electrode after application of voltage. 25 multiple, independent cells (10×10×0.5 mm) separated from each other by 1 mm of PLA and forming a 5 by 5 grid cell are located below the electrode being tested and are connected to a resistor with a known resistance value R. A data acquisition apparatus is used to read the voltage V on the known resistor, allowing to calculate the voltage drop on the electrode area located on the cell (input voltage: 5V). FIG. 7B shows tested locations for a self-gripping electrode on a prototype electrode.

Figure 7C:
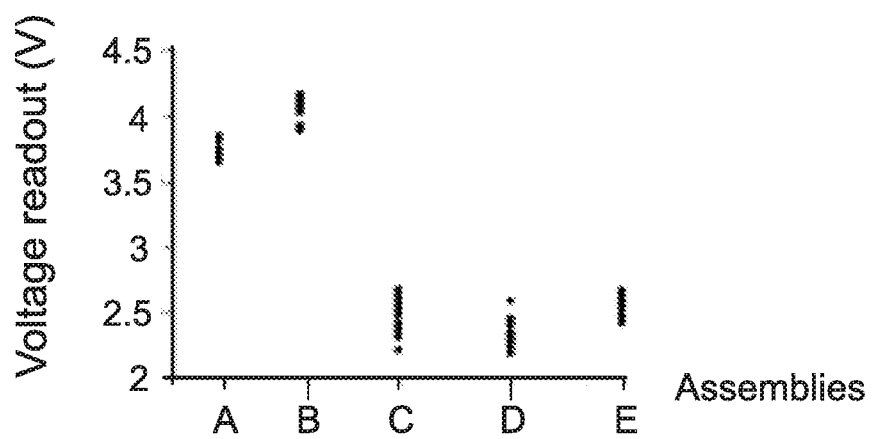

FIG. 7C shows voltage readouts for different tested systems, including a commercial electrode with its plug connector and a self-gripping connector attached to a prototype, custom electrode on the three different positions shown in FIG. 7B. In this experiment, the custom electrode comprises a gel layer with aluminium substrate.

The tested systems of the experiment illustrated in FIG. 7C are the following:
assemblies "A" and "B": commercial electrode equipped with a plug connector;
Assembly "C": experimental apparatus with a gripping connector attached to the electrode on position 1;
Assembly "D": experimental apparatus with a gripping connector attached to the electrode on position 2;
Assembly "E": experimental apparatus with a gripping connector attached to the electrode on position 3.

The conducted test shows the better efficacy and the efficiency of a connector having the gripping means of the invention, with respect to available commercial connectors and electrodes.

In particular, the conducted test proves the versatility and the single-hand usability of the proposed solution as the connector assembly is capable to homogeneous spread an electrical charge on the operational contact surface of an electrode, without requiring a precise positioning (alignment) with respect to the electrode.

LIST OF REFERENCE NUMERALS

100 Assembly for delivering electrical currents to and/or sensing electrical signals from a skin portion
1 Electrode
2 Electrical conductive portion
23 Proximal electrical conductive layer
24 Intermediate electrical conductive layer
25 Distal electrical conductive layer
26 Conductive portions/islands
201 Flat surface for contacting skin
3 Electrical insulating stratum
40 Conductor assembly
4 Connector or connector assembly
5 Connector body
6 Electrical conductor
7 Electrical insulator
8 Electrically conductive gripping elements
80 Elongated body
81 Longitudinal axis of the body
10 Safety release mechanism
11,11a-c Sharpened end
111,112 Longitudinal axis of a portion of the sharpened portion
12 Lead wire or conductor
13 electrode-detached configuration of the connector
14 prepared-for-attachment configuration of the connector
15 electrode-attached configuration of the connector
16 prepared-for-detachment configuration of the connector
17 Manipulating means
18 Retaining nibs
19 Magnet
20 Forces for deforming the resilient portion of the connector
121 Flat protrusion
122 Hole
123 Base
150 Surface of the connector
200 Skin portion
a Angle between the longitudinal axes of the body and of sharpened end

The invention claimed is:

1. A connector assembly for electrically connecting an electrode to a monitoring and/or stimulating device; whereby the electrode has an essentially flat conductive portion arranged to contact a skin portion of an individual, and an insulating stratum covering the conductive portion; the connector assembly comprising electrical conductive protuberances having sharpened elements so to pierce the conductive portion and/or the insulating stratum of the electrode and to engage themselves inside the electrical conductive portion of the electrode, wherein the assembly further comprises a portion configured to take a configuration in response to an external force so as to modify the orientation of at least part of the sharpened elements for piercing the conductive portion and/or the insulating stratum of the electrode;
wherein said portion is a moveable portion being movable from a rest configuration to a second configuration in response to said external force;
wherein the sharpened elements, in the second configuration, are oriented essentially along parallel directions for piercing the conductive portion and/or the insulating stratum of the electrode; and wherein at least one of the sharpened elements, in the rest configuration, is oriented along a direction being inclined with respect to a direction of another of said sharpened elements for providing retaining when engaged inside the electrical conductive portion of the electrode.

2. The connector assembly according to claim 1, wherein the moveable portion or the resilient portion is arranged for being moveable or deformable in response to a pair of opposed forces applied to a first and second application points of the connector assembly.

3. The connector assembly according to claim 2, the moveable portion or the resilient portion being arranged for being moveable or deformable from the rest configuration to the second configuration in response of a force applied by fingers of the individual.

4. The connector assembly according to claim 3, wherein at least one of said sharpened elements comprises at least a substantially radially extending element for providing retaining when engaged inside the electrical conductive portion of the electrode.

5. The connector assembly according to claim 4, wherein at least one of said sharpened elements comprises an elongated body and a sharpened end.

6. The connector assembly according to claim 5, said sharpened end being conical-shaped, curved, or hook-shaped.

7. The connector assembly according to claim 6, wherein said sharpened end comprises an elongated portion with a longitudinal axis being inclined with respect to a longitudinal axis of the elongated body.

8. The conductor assembly of claim 1, wherein the sharpened elements, in the second configuration, are oriented essentially along perpendicular directions to the insulating stratum and the conductive portion.

9. The conductor assembly of claim 8, wherein at least one of the sharpened elements, in the rest configuration, is oriented along a direction being perpendicular with respect to the insulating stratum and the conductive portion.

10. The conductor assembly of claim 1, wherein the sharpened elements, in the second configuration, pierce the insulating stratum through to the conductive portion.

11. The conductor assembly of claim 10, wherein the sharpened elements, in the second configuration, pierce the conductive portion without contacting the skin portion.

12. A connector assembly for electrically connecting an electrode to a monitoring and/or stimulating device; whereby the electrode has an essentially flat conductive portion arranged to contact a skin portion of an individual, and an insulating stratum covering the conductive portion; the connector assembly comprising electrical conductive protuberances having sharpened elements so to pierce the conductive portion and/or the insulating stratum of the electrode and to engage themselves inside the electrical conductive portion of the electrode, wherein the assembly further comprises a portion configured to take a configuration in response to an external force so as to modify the orientation of at least part of the sharpened elements for piercing the conductive portion and/or the insulating stratum of the electrode;
wherein said portion is a moveable portion being movable from a rest configuration to a second configuration in response to said external force;
wherein the sharpened elements, in the second configuration, are oriented essentially along parallel directions to each other for piercing the conductive portion and the insulating stratum of the electrode; wherein the sharpened elements, in the second configuration, are oriented essentially along perpendicular directions to the insulating stratum and the conductive portion; and wherein at least one of the sharpened elements, in the rest configuration, is oriented along a direction being inclined with respect to a direction of another of said sharpened elements for providing retaining when engaged inside the electrical conductive portion of the electrode.

13. The connector assembly according to claim 12, wherein the moveable portion or the resilient portion is arranged for being moveable or deformable in response to a pair of opposed forces applied to a first and second application points of the connector assembly.

14. The connector assembly according to claim 13, the moveable portion or the resilient portion being arranged for being moveable or deformable from the rest configuration to the second configuration in response of a force applied by fingers of the individual.

15. The connector assembly according to claim 12, wherein at least one of said sharpened elements comprises at least a substantially radially extending element for providing retaining when engaged inside the electrical conductive portion of the electrode.

16. The connector assembly according to claim 15, wherein at least one of said sharpened elements comprises an elongated body and a sharpened end.

17. The connector assembly according to claim 16, said sharpened end being conical-shaped, curved, or hook-shaped.

18. The connector assembly according to claim 16, wherein said sharpened end comprises an elongated portion with a longitudinal axis being inclined with respect to a longitudinal axis of the elongated body.

* * * * *